United States Patent
Heidl et al.

(10) Patent No.: US 11,753,440 B2
(45) Date of Patent: Sep. 12, 2023

(54) METHODS FOR THE SYNTHESIS OF ARGININE-CONTAINING PEPTIDES

(71) Applicant: DSM IP Assets B.V., Heerlen (NL)

(72) Inventors: Marc Heidl, Kaiseraugst (NL); Piero Geotti-Bianchini, Kaiseraugst (NL)

(73) Assignee: DSM IP ASSETS B.V., Heerlen (NL)

( * ) Notice: Subject to any disclaimer, the term of this patent is extended or adjusted under 35 U.S.C. 154(b) by 263 days.

(21) Appl. No.: 15/734,751

(22) PCT Filed: Jun. 5, 2019

(86) PCT No.: PCT/EP2019/064676
§ 371 (c)(1),
(2) Date: Dec. 3, 2020

(87) PCT Pub. No.: WO2019/234108
PCT Pub. Date: Dec. 12, 2019

(65) Prior Publication Data
US 2021/0230220 A1 Jul. 29, 2021

(30) Foreign Application Priority Data
Jun. 5, 2018 (EP) .................................... 18176102

(51) Int. Cl.
*A61K 38/00* (2006.01)
*C07K 5/11* (2006.01)
*C07K 1/06* (2006.01)
*C07K 5/078* (2006.01)
*C07K 5/09* (2006.01)
*C07K 5/107* (2006.01)
*C07K 5/10* (2006.01)

(52) U.S. Cl.
CPC ............ *C07K 5/1019* (2013.01); *C07K 1/064* (2013.01); *C07K 5/06156* (2013.01); *C07K 5/0817* (2013.01); *C07K 5/1016* (2013.01); *C07K 5/1027* (2013.01)

(58) Field of Classification Search
CPC .. C07K 1/064; C07K 5/06156; C07K 5/0817; C07K 5/1016; C07K 5/1019; C07K 5/1027; C07K 7/06; Y02P 20/55
See application file for complete search history.

(56) References Cited

U.S. PATENT DOCUMENTS 6,822,074 B1 * 11/2004 Jonczyk .................. C07K 7/64
530/335

FOREIGN PATENT DOCUMENTS

JP       2017203014 A  * 11/2017
WO      2010/033254      3/2010

OTHER PUBLICATIONS

English language translation of JP 2017203014 obtained by Espacenet (Year: 2017).*
International Search Report for PCT/EP2019/064676 dated Jul. 3, 2019, 5 pages.
Written Opinion of the ISA for PCT/EP2019/064676 dated Jul. 3, 2019, 8 pages.
Anonymous et al., "Cleavage deprotection and isolation of peptides after fmoc synthesis", Applied Biosystems, May 1, 1998, pp. 1-12.
Beck-Singer et al., "Sulfonation of Arginine Residues as Side Reaction in FMOC-Peptide Synthesis", International Journal of Peptide and Protein Research, vol. 38, No. 1, Jul. 1, 1991, pp. 25-31.
Carpino et al., "The 2,2,4,6,7-pentamethyldihydrobenzofuran-5-sulfonyl group (Pbf) as arginine side chain protectant", Tetrahedron Letters, vol. 34, No. 49, Dec. 3, 1993, pp. 7829-7832.
Thompson et al., "Synthesis of Peptide Amides Using FMOC-Based Solid-Phase Procedureson 4-Methylbenzhydrolamine Resins", International Journal of Peptide and Protein Research, vol. 46, No. 2, Aug. 1, 1995, pp. 174-180.
Yajima et al., "Studies on peptides. L. Acidolysis of protecting groups in peptide chemistry by fluorosulphonic acid and methanesulphonic acid", Chemical and Pharmaceutical Bulletin, vol. 23, No. 5, Jan. 1, 1975, pp. 1164-1166.
King et al., "A cleavage method which minimizes side reactions following Fmoc solid phase peptide synthesis", International Journal of Peptide & Protein Research, vol. 36, No. 3, Sep. 1990.

* cited by examiner

*Primary Examiner* — Aradhana Sasan
*Assistant Examiner* — Mercy H Sabila
(74) *Attorney, Agent, or Firm* — NIXON & VANDERHYE P.C.

(57) ABSTRACT

Methods for the synthesis of arginine-containing peptides are provided. The methods include a deprotection step that minimizes the transfer of by-products deriving from cleaved sulfonyl-5 based side chain protecting groups from arginine to amino acids carrying electron rich side chains.

19 Claims, No Drawings

METHODS FOR THE SYNTHESIS OF ARGININE-CONTAINING PEPTIDES

This application is the U.S. national phase of International Application No. PCT/EP2019/064676 filed Jun. 5, 2019 which designated the U.S. and claims priority to EP Patent Application No. 18176102.4 filed Jun. 5, 2018, the entire contents of each of which are hereby incorporated by reference.

Methods for the synthesis of arginine-containing peptides are provided. The novel methods include a deprotection step that minimizes the transfer of cleaved by-products deriving from sulfonyl-based side chain protecting groups from arginine to amino acids carrying electron rich side chains.

Peptides and amino acids from which peptides are synthesized tend to have reactive side groups. Undesired reactions at side groups of a peptide produce undesirable by-products, sometimes in significant quantities. These by-products and reactions can seriously impair yield or even ruin the product being synthesized from a practical perspective. To minimize these side reactions, it is thus conventional practice to appropriately mask reactive side groups of reactants to help ensure that the desired reaction occurs. After completion of the peptide synthesis, these side chain protecting groups, however, must be removable quantitatively in order not to negatively affect peptide quality or yield.

To incorporate arginine into a peptide generally methoxytrimethylbenzene sulfonyl-(Mtr-), 2,2,5,7,8-pentamethyl-chroman-6-sulfonyl-(Pmc-), or 2,2,4,6,7-pentamethyl-dihydrobenzofuran-5-sulfonyl-(Pbf-) protected arginine is used. It has, however, been demonstrated that if the final peptide further comprises amino acids carrying electron rich side chains such as histidine and/or tryptophan, cleaved sulfonyl-based side chain protecting groups from the arginine readily react with electron-rich side chains of other residues, resulting in significant amounts of unwanted by-products. Furthermore, the use of the above-mentioned protecting groups requires extended deprotection times or harsher final deprotection conditions which may also negatively affect the peptide quality and/or yield.

To avoid problems associated with arginine side chain protecting groups, side chain unprotected, alpha amino protected arginine is also available for use in peptide synthesis. However, as discussed above, undesired reactions at side chain groups produces undesirable by-products. In the case of arginine, the tri-functional guanidino side chain is strongly nucleophilic and can be reactive in conditions wherein either side chain unprotected arginine is free in solution (not coupled to the nascent peptide) or coupled to the nascent peptide. Thus, the use of side chain protected arginine is still generally preferred.

Thus, there is an ongoing need of an efficient and improved method for the deprotection of the side chain protecting groups of arginine in peptides further comprising amino acids carrying electron rich side chains.

Surprisingly it has now been found that the preparation of a certain pre-dispersion of a peptide comprising a side chain protected arginine and an amino acid carrying an electron rich side chain followed by mixing said pre-dispersion with an acid which is able to cleave the Mtr-, Pmc- or Pbf-significantly reduces the formation of by-products.

Thus, in a first embodiment the present invention relates to a method for deprotecting a peptide comprising a Mtr-, Pmc- or Pbf-side chain protected arginine and at least an amino acid carrying an electron rich aromatic side chain, said method comprising the steps of:

a.) solubilizing the peptide in a mixture (also referred to herein as solvent mixture) of at least one aprotic organic solvent, a thiol scavenger, and either a protic solvent or an acid which is not able to remove the arginine-protecting group or a mixture thereof, followed by b.) mixing the solution obtained in step a.) with a mixture (also referred to herein as cleavage mixture) of an acid which is not able to remove the arginine protecting group and an acid which is able to remove the arginine-protecting group with the proviso that the total amount (by moles) of the acid which is not able to remove the arginine-protecting group used in step a.) and b.) is higher than the amount of the acid which is able to remove the arginine-protecting group.

It is well understood, that the present invention encompasses the peptides as optically pure isomers, such as e.g. as pure enantiomers or stereoisomers, as well as mixtures of different isomers, such as e.g. as racemates, or mixtures of diastereoisomers.

The term "side chain" of an amino acid as used herein generally refers to that portion of the amino acid attached to the common $NH_2$-$\overset{|}{C}H$—COOH backbone or me respective amino acids. For instance, the side chain of serine is —$CH_2$—OH and the side chain of alanine is —$CH_3$.

The term "an acid which is not able to remove the arginine-protecting group" refers to an acid which is not able to quantitatively remove (i.e. up to 95-100%) the arginine protecting group (such as in particular trifluoroacetic acid, acetic acid or formic acid) under the given reaction conditions as outlined below and illustrated in the examples.

The term "an acid an acid which is able to remove the arginine-protecting group" refers to an acid which is able to quantitatively remove the arginine protecting group (such as in particular methanesulfonic acid) under the given reaction conditions as outlined below and illustrated in the examples.

Preferred electron rich side chains in all embodiments of the present invention are 'aryl$C_1$-$C_6$ alkyl groups' and/or 'heteroaryl$C_1$-$C_6$ alkyl groups'.

The term "aryl$C_1$-$C_6$ alkyl group" as used herein refers to a —$C_1$-$C_6$ alkyl-aryl group (i.e. to a $C_1$-$C_6$alkyl group which is substituted by an aryl group, i.e. the attachment point is the alkyl group), wherein the term "aryl" refers to an aromatic substituent containing 5 to 15 carbon atoms and containing a single aromatic ring or multiple aromatic rings which are fused together, directly linked or indirectly linked (such that the different aromatic rings are bound to a common group such as a methylene or ethylene group). Particularly advantageous aryl groups according to the present invention contain 6 to 12 carbon atoms containing a single aromatic ring or multiple aromatic rings which are fused together or directly linked. Most preferred aryl residues in all embodiments of the present invention are phenyl, naphthyl and biphenyl. Particularly advantageous aryl$C_1$-$C_6$ alkyl groups in all embodiments of the present invention are aryl$C_1$-$C_2$ alkyl groups such as in particular phenyl(m)ethyl or naphthyl(m)ethyl.

The term "heteroaryl$C_1$-$C_6$ alkyl groups" refers to a —$C_1$-$C_6$ alkyl-heteroaryl (i.e. to a $C_1$-$C_6$alkyl group which is substituted by a heteroaryl group, i.e. the attachment point is the alkyl group), wherein the term "heteroaryl" refers to a 5-, 6- or 7-membered aromatic ring containing one or more heteroatoms, viz., N, O or S; these heteroaromatic rings may be fused to other aromatic systems. Particularly preferred heteroaromatic rings encompass imidazole, indole, pyridine and quinoline.

The aryl respectively heteroaryl residues may, independently of each other, be unsubstituted or substituted with one or more substituents. In all embodiments of the present invention, such substituents are preferably selected from halogen, hydroxy, nitro, cyano, $C_1$-$C_6$ alkyl, $C_1$-$C_6$ alkoxy and $C_1$-$C_6$ alkanoyloxy. More preferably in all embodiments of the present invention the aryl respectively heteroaryl residues are, independently of each other, unsubstituted or substituted with one or two substituents selected from the group consisting of F, Cl, hydroxy, cyano, $C_1$-$C_3$ alkyl, $C_1$-$C_3$ alkoxy and $C_1$-$C_3$ alkanoyloxy such as in particular unsubstituted or substituted with one or two substituents selected from the group consisting of F or hydroxy. Most preferably, in all embodiments of the present invention, the aryl and the heteroaryl residues are unsubstituted or substituted with F, hydroxy or nitro.

In all embodiments of the present invention particular advantageous aryl$C_1$-$C_6$ alkyl group are aryl$C_1$-$C_2$ alkyl groups, which are preferably unsubstituted or substituted with one or two substituents selected from the group of F (fluoro), hydroxy (OH) or nitro ($NO_2$). Most preferred aryl$C_1$-$C_6$ alkyl group in all embodiments of the present invention are phenyl(m)ethyl, 4-hydroxyphenyl(m)ethyl, 3-nitro-4-hydroxyphenyl(m)ethyl or naphthyl(m)ethyl such as in particular phenylmethyl, 4-hydroxyphenyl(m)ethyl, 3-nitro-4-hydroxyphenylmethyl or 1- or 2-naphthylmethyl.

In all embodiments of the present invention most preferred heteroaryl$C_1$-$C_6$ alkyl group are heteroaryl$C_1$-$C_2$ alkyl groups such as (1H-indol-3-yl)(m)ethyl, (1H-imidazol-4-yl)(m)ethyl, (pyridin-2-yl)(m)ethyl, (pyridin-3-yl)(m)ethyl, (quinolin-2-yl)(m)ethyl and (quinolin-3-yl)(m)ethyl groups which are preferably unsubstituted or substituted with one or two substituents selected from the group of F (fluoro), hydroxy (OH) or nitro ($NO_2$). Most preferred in all embodiment of the present invention are (1H-indol-3-yl)(m)ethylene, or (1H-imidazol-4-yl)(m)ethylene.

In all embodiments the most preferred amino acids carrying an electron rich aromatic side chain are selected from the group of D/L-histidine, D/L-tryptophan, 6-fluoro-tryptophan, 5-hydroxy-tryptophan, D/L-phenylalanine, D/L-tyrosine, D/L-m-nitrotyrosine, D/L-O-ethyl-tyrosine, D/L-3-(2-naphthyl)-alanine). Particularly advantageous amino acids carrying an electron rich aromatic side chain are selected from the group of D/L-Histidine, D/L-Phenylalanine, D/L-tyrosine and D/L-tryptophan as well as O—$C_1$-$C_6$-alkylated D/L-tyrosine; m/p-Cl/Br/I-D/L-phenylalanine; and 4/-5-/6-/7-OH/F/Cl/Br/methyl-D/L-tryptophan. Most preferred electron rich side chains in all embodiments of the present invention are the ones of D/L-histidine, D/L-tryptophan, D/L-tyrosine, D/L-tryptophan, 5-hydroxy D/L-tryptophan and 6-fluoro D/L-tryptophan. It is well understood that the term D/L encompasses the respective D-amino acids, L-amino acids as well as mixtures thereof.

In all embodiments of the present invention most preferably the peptide comprising a Mtr-, Pmc- or Pbf-side chain protected arginine also contains at least an amino acid carrying an electron rich aromatic side chain selected from the group of D/L-histidine, D/L-tryptophan, tyrosine, D/L-6-fluoro-tryptophan and D/L-5-hydroxy-tryptophan as then the improvement in the purity of the crude product and consequently the achievable yield after product isolation is particularly pronounced.

In all embodiments of the present invention particularly preferred peptides are peptides comprising a Mtr- or Pbf-side chain protected arginine, most preferably a Pbf-side chain protected arginine.

Particularly suitable aprotic solvents in all embodiments of the present invention are aromatic hydrocarbons, which are liquid at ambient temperature (i.e. 20° C.) or $C_{1-6}$-halogenoalkanes, such as in particular $C_{1-6}$-fluoro and/or chloroalkanes, e.g. chloroform, dichloromethane, dichloroethane, 1,1-difluoroethane and/or acetonitrile as well as mixtures thereof and without being limited thereto.

Particularly preferred aromatic hydrocarbon liquids in all embodiments of the present invention are $C_{1-3}$-alkylbenzenes, such as preferably benzene, toluene or xylene, most preferably toluene.

Particularly preferred $C_{1-6}$-halogenoalkanes liquids in all embodiments of the present invention are $C_{1-3}$-halogenoalkanes, such as more preferably $C_{1-3}$-chloroalkanes, most preferably dichloromethane.

A further suitable aprotic solvent to be used according to the present invention is acetonitrile, preferably in admixture with dichloromethane.

In all embodiments of the present invention, the amount of the aprotic solvent is selected such that the peptide to be deprotected is capable to be solubilized therein, preferably as such or at least in the presence of the thiol scavenger, the protic solvent and/or the acid which is not able to remove the arginine-protecting group at a temperature selected in the range from −10° C. to 40° C., preferably from 0° C. to 30° C., even more preferably from 10 to 25° C. Further preferred temperature ranges include the range from 15 to 30° C., from 15 to 25° C., from 18 to 25° C. and from 18 to 22° C. Even more preferably, the (total) amount of the aprotic solvent is at least 1 ml/g of peptide (i.e. 1 ml of solvent per gram of peptide), preferably at least 2 ml/g of peptide, most preferably at least 2.5 ml/g of peptide. Preferably, in all embodiments of the present invention, the amount of the aprotic solvent is selected in the range from 1 to 100 ml/g of peptide, more preferably in the range from 2 to 10 ml/g of peptide, most preferably in the range of 2.5 to 7 ml/g of peptide.

Particularly suitable protic solvents in all embodiments of the present invention are selected from the group of water and alcohols, preferably from water and linear, branched or cyclic alkyl alcohols, such as e.g. methanol, ethanol, propanol, isopropanol, butanol, isobutanol and cyclohexanol without being limited thereto. Most preferred in all embodiments of the present invention is the use of methanol, ethanol and water as well as mixtures thereof.

Particular suitable protic solvents in all embodiments of the present invention are water and $C_{1-4}$-alkyl alcohols. The most preferred protic solvents in all embodiments according to the present invention are water, methanol and ethanol such as in particular methanol and ethanol as well as mixtures thereof.

If present, the total amount of the protic solvent(s) is preferably selected in the range from 0.01 to 7% (v/v), more preferably in the range from 0.5 to 5% (v/v), most preferably in the range from 1 to 5% (v/v), based on the total volume of the solution added to dissolve the peptide. The term (v/v) refers to volume percent (vol %), i.e. the vol-% of the protic solvent based on the total volume of the solvent mixture in step a.))

Particularly suitable acids which are not able to remove the arginine-protecting group are carboxylic acids. Particularly preferred acids which are not able to remove the arginine-protecting group in all embodiments of the present invention are selected from the group of formic acid, acetic acid and trifluoroacetic acid as well as any mixture thereof. Most preferred in all embodiments is the use acetic acid and/or trifluoroacetic acid such as in particular trifluoroacetic acid.

If present, the total amount of acid(s) which are not able to remove the arginine-protecting group in step a.), in all embodiments of the present invention, is preferably selected in the range from 3 to 50% (v/v), more preferably in the range from 5 to 40%, most preferably in the range from 5 to 30% (v/v), such as in the range of 5 to 15% (v/v) or in the range from 7 to 12% (v/v), based on the total volume of the solution added to dissolve the peptide (i.e. based on the total volume of the solvent mixture).

In all embodiments of the present invention, the total amount of acid(s) which are not able to remove the arginine-protecting group in step a.) is preferably selected in the range from 3 to 25 mol-equivalents, more preferably in the range from 5 to 20 mol-equivalents, most preferably in the range of 5 to 15 mol-equivalents, based on each (individual) protected arginine moiety.

It is furthermore preferred that the time to solubilize the peptide in step a.) is not exceeding 1 hour. More preferably the time to solubilize the peptide in step a.) is selected in the range of 5 minutes to one hour, more preferably in the range from 10 minutres to 45 minutes, most preferably in the range of 15 minutes to 30 minutes.

Additonally, in all embodiments of the present invention, the reaction temperature in step a.) is preferably selected in the range of 15 to 30° C., more preferably in the range of 15 to 25° C., most preferably in the range of 18 to 25° C., such as in the range of 18 to 22° C.

It is well known to a person skilled in the art that the amounts of acid(s) and/or conditions for step a.) as outlined above and illustrated in the examples are not sufficient to quantitatively remove the arginine protecting groups.

It is furthermore well understood, that in step a.) no acid which is able to remove the arginine-protecting group such as methanesulfonic acid may be present as this significantly increases the formation of alkylated or sulfonated side products, reducing the purity of the crude product and thus lowering the isolated yield in free peptide accordingly. The mixture may, however, e.g. contain further scavengers as defined below.

It is however particularly advantageous if in step a.) the peptide is solubilized in a solvent mixture consisting essentially of at least one aprotic organic solvent, a thiol scavenger, and either a protic solvent or an acid which is not able to remove the arginine-protecting group or a mixture thereof with all the definitions and preferences as given herein.

The term 'consisting essentially of' as used according to the present invention means that the total amount of the listed ingredients ideally sums up to 100 wt.-%. It is however not excluded that small amounts of impurities or additives may be present, with the proviso that the total amount of such impurities or additives is preferably less than 3 wt.-%, more preferably less than 2 wt.-%, most preferably less than 1 wt.-%.

Particularly suitable acids which are able to remove the arginine-protecting group are sulfonic acids, such as methane sulfonic acid (MSA), trifluoromethane sulfonic acid (triflic acid), benzene sulfonic acid or p-toluene sulfonic acid. Most preferably, in all embodiments of the present invention the acids which is able to remove the arginine-protecting group is MSA.

Suitable thiol scavengers according to the present invention are all thiol scavengers commonly used in peptide synthesis. Particular preferred thiol scavengers in all embodiments of the present invention are aliphatic thiols (alkylthiols), more preferably dodecanethiol. It is however not excluded that other scavengers, may be added to step a.) together with the thiol scavenger, such as in particular trialkylsilanes (more preferably 014-trialkylsilanes), such as, triethylsilane, triisopropylsilane) and/or water.

Most preferred in all embodiments of the present invention is the use of dodecanethiol as scavenger, optionally in the presence of an additional scavenger selected from a trialkylsilane (more preferably a $C_{1-4}$-trialkylsilane) and water as well as mixtures thereof, more preferably selected from triethylsilane, triisopropylsilane and water as well as mixtures thereof. Most preferred in all embodiments according to the present invention is the use of dodecanethiol, either alone or in combination with triisopropylsilane and/or water.

The total amount of scavenger is preferably selected in the range from 0.1 to 100 mol-equivalents relative to the number of arginine-protecting groups present in the peptide to be deprotected, preferably from 1 to 20 mol-equivalents, even more preferably from 2 to 10 mol-equivalents, most preferably from 3 to 6 mol-equivalents.

In a particularly advantageous embodiment, in step a.) an acid which is not able to remove the arginine-protecting group, optionally in the presence of a protic solvent, with all the definitions and preferences as given herein, is used. The amount of the protic solvent is preferably selected in the range of 0 to 20% (v/v), preferably in the range of 0 to 15% (v/v), most preferably in the range of 0 to 10% (v/v), such as in the range of 0 to 5% (v/v), based on the amount of acid which is not able to remove the arginine-protecting group.

The amount of the acid which is not able to remove the arginine protecting groups such as preferably formic acid, acetic acid and/or trifluoroacetic acid in step b.) in all embodiments of the present invention is preferably selected in the range from 75 to 250 mol-equivalents, more preferably in the range from 80 to 200 mol-equivalents, most preferably from 90 to 175 mol-equivalents such as from 100 to 150 mol equivalents based on each (individual) protected arginine moiety.

The amount of the acid which is able to remove the arginine protecting groups such as preferably methanesulfonic acid in step b.) in all embodiments of the present invention is preferably selected in the range from 1 to 20 mol-equivalents, more preferably in the range from 2 to 12 mol-equivalents, most preferably from 3 to 10 mol-equivalents such as from 5 to 8 mol equivalents based on each (individual) protected arginine moiety.

Additonally, in all embodiements of the present invention, the reaction temperature in step b.) is preferably selected in the range of 15 to 30° C., more preferably in the range of 15 to 20° C., most preferably in the range of 18 to 25° C., such as in the range of 18 to 22° C.

The reaction time in step b.) is not critical. However, it is preferred that the reaction time in step b.) is not exceeding 5 hours. More preferably the reaction time is selected in the range of 15 minutes to 3 hours, more preferably in the range from 30 minutes to 2.5 hours, most preferably in the range of 45 minutes to 2 hours.

Advantageously, in all embodiments of the present invention, the the amount (molar) of the acid which is not able to remove the arginine protecting group (such as preferably formic acid, acetic acid and/or trifluoroacetic acid) used in step b.) is higher than the amount (molar) of the acid which is able to remove the arginine-protecting group (such as preferably methane sulfonic acid). Even more advantageously the molar ratio of the the acid which is not able to remove the arginine protecting group (such as preferably formic acid, acetic acid and/or trifluoroacetic acid) to the acid which is able to remove the arginine-protecting group (such as preferably methane sulfonic acid) in step b.) is selected in the range of 50:1 to 5:1, more preferably in the range of 30:1 to 10 to 1, most preferably in the range of 20 to 1 to 10:1.

It is furthermore advantageous if, the molar ratio of the amount (total) of the acid which is not able to remove the arginine protecting group (such as preferably formic acid, acetic acid and/or trifluoroacetic acid) used in step a.) and b.) and the amount of the acid which is able to remove the arginine-protecting group (such as preferably methane sulfonic acid) used in step b.) is selected in the range of 100:1 to 10:1, preferably in the range from 50:1 to 12:1, more preferably in the range from 30:1 to 15:1, most preferably in the range from 25:1 to 18:1. Further suitable ranges include 25:1 to 12:1 or 20:1 to 15:1.

In a particularly advantageous embodiment the solvent mixture in step a.) consists of
 i.) 1 to 100 ml, preferably 2 to 10 ml, most preferably 2.5 to 7 ml of an aprotic solvent/per g of peptide,
 ii.) 0.1 to 100 mol-equivalents, preferably 1 to 20 mol-equivalents, most preferably 2 to 10 mol-equivalents, based on each (individual) protected arginine moiety, of a scavenger, wherein the scavenger is dodecanethiol or a mixture of dodecanethiol with trialkylsilanes and/or water,
 iii.) 3 to 25 mol-equivalents, preferably 5 to 20 mol-equivalents, most preferably 5 to 15 mol-equivalents, based on each (individual) protected arginine moiety, of formic acid, acetic acid and/or trifluoroacetic acid, and
 iv.) 0 to 15 vol-%, preferably 0 to 10 vol-%, most preferably 0 to 5 vol-%, based on the amount of formic acid, acetic acid and/or trifluoroacetic acid, of a protic solvent.

Even more preferably, the solvent mixture in step a.) consists of
 i.) 1 to 100 ml, preferably 2 to 10 ml, most preferably 2.5 to 7 ml of benzene, toluene, xylene, dichloromethane and/or acetonitrile/per g of peptide,
 ii.) 0.1 to 100 mol-equivalents, preferably 1 to 20 mol-equivalents, most preferably 2 to 10 mol-equivalents, based on each (individual) protected arginine moiety, of a scavenger, wherein the scavenger is dodecanethiol or a mixture of dodecanethiol with triethylsilane, triisopropylsilane and/or water,
 iii.) 3 to 25 mol-equivalents, preferably 5 to 20 mol-equivalents, most preferably 5 to 15 mol-equivalents, based on each (individual) protected arginine moiety, of acetic acid and/or trifluoroacetic acid, and
 iv.) 0 to 15 vol-%, preferably 0 to 10 vol-%, most preferably 0 to 5 vol.-%, based on the amount of acetic acid and/or trifluoroacetic acid, of methanol and/or ethanol.

Most preferably, the solvent mixture in step a.) consists of
 i.) 1 to 100 ml, preferably 2 to 10 ml, most preferably 2.5 to 7 ml of toluene, dichloromethane or a mixture of dichloromethane and acetonitrile/per g of peptide,
 ii.) 0.1 to 100 mol-equivalents, preferably 1 to 20 mol-equivalents, most preferably 2 to 10 mol-equivalents, based on each (individual) protected arginine moiety, of a scavenger, wherein the scavenger is dodecanethiol or a mixture of dodecanethiol with triisopropylsilane and/or water,
 iii.) 0 to 15 vol-%, preferably 0 to 10 vol-%, most preferably 0 to 5 vol.-%, based on the amount of acetic acid and/or trifluoroacetic acid, of methanol and/or ethanol, and
 iv.) 3 to 25 mol-equivalents, preferably 5 to 20 mol-equivalents, most preferably 5 to 15 mol-equivalents, based on each (individual) protected arginine moiety, of acetic acid and/or trifluoroacetic acid.

In all embodiments of the present invention the cleavage mixture in step b.) preferably consists of
 i.) 75 to 250 mol-equivalents, preferably 80 to 200 mol-equivalents, more preferably 90 to 175 mol-equivalents, most preferably 100 to 150 mol equivalents, based on each (individual) protected arginine moiety, of formic acid, acetic acid and/or trifluoroacetic acid, and
 ii.) 1 to 20 mol-equivalents, preferably 2 to 12 mol-equivalents, more preferably from 3 to 10 mol-equivalents, most preferably 5 to 8 mol equivalents based on each (individual) protected arginine moiety, of a sulfonic acid, preferably methanesulfonic acid.

Even more preferably, in all embodiments of the present invention the cleavage mixture in step b.) consists of
 i.) 75 to 250 mol-equivalents, preferably 80 to 200 mol-equivalents, more preferably 90 to 175 mol-equivalents, most preferably 100 to 150 mol equivalents, based on each (individual) protected arginine moiety, of acetic acid and/or trifluoroacetic acid, and
 ii.) 1 to 20 mol-equivalents, preferably 2 to 12 mol-equivalents, more preferably from 3 to 10 mol-equivalents, most preferably 5 to 8 mol equivalents based on each (individual) protected arginine moiety, of methanesulfonic acid.

Most preferably, in all embodiments of the present invention the cleavage mixture in step b.) consists of
 i.) at most 250 mol-equivalents, preferably at most 200 mol-equivalents, more preferably at most 175 mol-equivalents, most preferably at most 150 mol equivalents, based on each (individual) protected arginine moiety, of acetic acid and/or trifluoroacetic acid, and
 ii.) 1 to 20 mol-equivalents, preferably 2 to 12 mol-equivalents, more preferably from 3 to 10 mol-equivalents, most preferably 5 to 8 mol equivalents, based on each (individual) protected arginine moiety, of methanesulfonic acid,
 with the proviso, that the molar ratio of the amount acetic acid and/or trifluoroacetic acid used in step a.) and b.) and the amount of methane sulfonic acid used in step b.) is selected in the range of 100:1 to 10:1, preferably in the range from 50:1 to 12:1, more preferably in the range from 30:1 to 15:1, most preferably in the range from 25:1 to 18:1.

It is well understood, that the acids (i.e. the acid which is not able to remove the arginine protecting group such as in particular the formic acid, acetic acid and/or trifluoroacetic acid and the acid which is able to remove the arginine-protecting group such as in particular the methanesulfonic acid) which are used in step b.) can either be admixed seperately with the solution from step a.). Preferably, however, these acids are admixed before being admixed with the solution from step a.). Most preferably, in all embodiments of the present invention, the cleavage mixture is a cleavage solution consisting of acetic acid and/or trifluoroacetic acid and methanesulfonic acid with all the definitions and preferences as given herein.

In all embodiments of the present invention the peptide comprising a Mtr-, Pmc- or Pbf-side chain protected arginine and at least an amino acid carrying an electron rich aromatic side chain is a a di- to a hexapeptide, i.e. a dipeptide, a tripeptide, a tetrapeptide, a pentapeptide or a hexapeptide.

In a further preferred embodiment the Mtr-, Pmc- or Pbf-side chain protected arginine and the at least an amino acid carrying an electron rich aromatic side chain are seperated by at most 3 amino acids, preferably by at most two amino acids and more preferably by at most one amino acid. In all embodiments of the present invention however, the electron rich amino acid is most preferably directly adjacent to the Mtr-, Pmc- or Pbf-side chain protected arginine.

Even more preferably, in all embodiments of the present invention the peptide is a peptide comprising at least one Pbf-protected arginine moiety and at least one amino acid moiety selected from the group of tyrosine, histidine and/or tryptophan which histidine, tyrosine respectively tryptophan moiety is preferably at most two, more preferably at most one, such as in particular directly adjacent to the protected arginine moiety. Particularly preferred tyrosine, histidine and/or tryptophan amino acids are histidine, tyrosine, tryptophan, 5-hydroxytryptophane and 6-fluoro tryptophan as well as mixtures thereof. It is well understood, that as mentioned above, the Pbf-protected arginine moiety as well as the amino acid moieties can be L- or D-configurated or be mixtures of both configurations (within the peptide).

Preferred peptides in all embodiments of the present invention are peptides comprising at least one Pbf-protected arginine and at least one amino acid selected from the group of histidine, tyrosine, tryptophan, 5-hydroxytryptophan and 6-fluoro tryptophan as well as mixtures thereof, more preferably, peptides comprising one Pbf-protected arginine and at least one amino acid selected from the group of histidine, tyrosine, tryptophan, 5-hydroxytryptophan and 6-fluoro tryptophan as well as mixtures thereof, such as in particular tri- to hexapeptides.

Particularly preferred peptides according to the present invention are Boc-Trp-Arg(Pbf)-OH, Ac-Arg(Pbf)-His(Trt)-Phe-OH, TFA-H-Tyr(tBu)-Arg(Pbf)-Pro-OH, Boc-rac-6FTrp-Gly-Arg(Pbf)-Glu(OtBu)-OH, Boc-Tyr(Et)-Arg(Pbf)-Ala-Phe-OH, Ac-5-(OH)Trp-Ala-Arg(Pbf)-Ser(tBu)-Leu-Phe-OH, Boc-Arg(Mtr)-Tyr(tBu)-Phe-OH, Boc-2Nal-Leu-Arg(Pbf)-Phe-OH, Ac-Arg(Pbf)-Met-m(NO$_2$)Tyr-Pro-OH and Bz-Gly-His(Trt)-D-Phe-Arg(Pbf)-D-Trp-N(Pr)$_2$.

The invention is further illustrated with reference to the following, non-limiting examples, in which all percentages are by weight based on total weight unless otherwise specified.

| Experimental part General Information Abbreviations used in the present application | |
|---|---|
| 2Nal | 3-(2-naphthyl)-alanine |
| 5(OH)Trp | 5-hydroxy-tryptophan |
| 6FTrp | 6-fluoro-tryptophan |
| Ac | acetyl |
| AcOEt | ethyl acetate |
| AcOH | acetic acid |
| Ala | alanine |
| Arg | arginine |
| Boc | tert-butyloxycarbonyl |
| tBu | tert-butyl |
| Bz | benzoyl |
| calcd | calculated |
| DCM | dichloromethane |
| DDCT | dodecanethiol |
| DMSO | dimethylsulfoxide |
| Et | ethyl |
| EtOH | ethanol |
| Glu | glutamic acid |
| Hex | n-hexane |
| Leu | leucine |
| MeCN | acetonitrile |
| MeOH | methanol |
| Met | methionine |

-continued

| Experimental part General Information Abbreviations used in the present application | |
|---|---|
| min | minute |
| MS | mass spectrometry |
| MSA | methanesulfonic acid |
| MTBE | methyl tert-butyl ether |
| Mtr | 4-methoxy-2,3,6-trimethylbenzene-sulfonyl |
| m(NO$_2$) Tyr | 3'-nitro-tyrosine |
| OtBu | tert-butyl ester |
| Pbf | 2,2,4,6,7-pentamethyl-l dihydrobenzofurane-5-sulfony |
| PDA | photodiode array |
| Phe | phenylalanine |
| PhMe | toluene |
| PhSMe | thioanisole (methyl phenyl sulphide) |
| Pr | propyl |
| Pro | proline |
| rac | raceme |
| rpm | runs per minute |
| Ser | serine |
| TFA | trifluoroacetic acid (≥99%) |
| THF | tetrahydrofurane |
| TIS | triisopropyl silane |
| Trt | trityl |
| Tyr | tyrosine |
| UPLC | ultra-high-performance liquid chromatography |

Materials and Methods

Analytical grade toluene was desiccated on sodium sulphate prior to use. MilliQ water was used. All other solvents and reagents were analytical grade or higher and used as received. Analytical chromatograms were measured on a Waters Acquity Ultra Performance Liquid Chromatography (UPLC), equipped with an Acquity HSS T3 100 Å, 1.8 µm 2.1×50 mm2 analytical column and a PDA detector operating in the 200-400 nm wavelength range. H$_2$O+0.02% TFA (A phase) and MeCN+0.02% TFA (B phase) were used as eluents, with a flow of 0.5 mL/min.

Low-resolution mass-spectra were measured on a Waters Acquity I-Class Ultra Performance Liquid Chromatography, equipped with an Acquity HSS T3 100 Å, 1.8 µm 2.1×50 mm2 analytical column and a PDA detector operating in the 200-400 nm wavelength range coupled to a Waters Single Quadrupole Detector mass spectrometer operating in positive electrospray ionization (ESI+) mode and detecting in the m/z range 100-1500. H$_2$O+0.04% HCOOH (A' phase) and MeCN+0.04% HCOOH (B' phase) were used as eluents, with a flow of 0.6 mL/min.

An Eppendorf 5415C centrifuge was used for centrifugation.

General Procedure

The peptides containing protected arginine were prepared either by solution-phase methods or by solid-phase methods and cleaved from the resin without removal of side- and N-terminal protecting groups, purified if necessary and dried in the drying cabinet prior to use. Purity of the starting material was determined by UPLC.

In the description of the final deprotection methods, molar equivalents and solvent volumes are referred to the amount of protected-arginine containing peptides considering their purity as determined by UPLC, where not otherwise stated.

To compare the results obtained with different deprotection methods, probes of the reaction mixtures (5-10 µL) were sampled after the same reaction times, diluted in 1 mL ice-cold 1:1 MTBE/Hex, the resulting suspensions were centrifugated at 10000-14000 rpm for 5 min, then decanted, the pellets were taken up in 1 mL ice-cold 1:1 MTBE/Hex, shaken, centrifugated (once or twice) at 10000-14000 rpm for 5 min, the resulting pellets were dissolved in 1 mL of a suitable solvent (methanol, 10% aqueous acetonitrile, or 90% aqueous acetonitrile, depending on the polarity of the deprotected peptide) and analyzed by UPLC. This procedure was repeated until probes sampled from the standard and the improved deprotection mixture displayed complete disappearance of the peak of the protected peptide and 51% of the Arg(Pbf)-containing deprotection intermediate.

For each peptide sequence tested, at least one probe was analyzed by UPLC-MS to confirm that the main peak corresponded to the desired deprotected peptide.

Comparison of Standard One-Step (Reference) and Improved Two-Step (Invention)

For each protected peptide mentioned in the examples 1-8 below, the same amount of material was treated with the standard and with the improved procedure, both described below.

Standard (reference) method: the protected peptide and a stirrer were given in a glass flask or vial. A cleavage mixture was prepared by mixing PhMe (2.8 mL/g), TFA (127 eq), DDCT (4 eq), MSA (7.1 eq). The cleavage solution was added to the protected peptide at once under stirring at RT (22° C.). The respective cleavage mixtures were stirred for the time given in the examples.

Method according to the invention: the protected peptide and a stirrer were given in a glass flask or vial. PhMe (2.5 mL/g), TFA (7.2 eq) and DDCT (4 eq) were mixed and given to the peptide under stirring. The mixture was stirred until a solution resulted; if, after several minutes stirring and short sonication, undissolved material remained, increasing amounts of TFA and/or PhMe were added in small portions under stirring until complete dissolution (peptide solution). A cleavage solution was prepared by mixing TFA (120 eq) and MSA (7.1 eq) in a round bottomed flask. The peptide solution was added dropwise with a syringe to the cleavage solution under stirring; the container of the peptide solution was rinsed with PhMe (0.28 mL/g) and rinsings solutions were added dropwise to the cleavage solution. The resulting mixtures were stirred for the time given in the examples.

The amount of desired free peptide in the resulting reaction mixtures was assessed by UPLC (and is expressed as area %) The identity of all products (reference and invention) was confirmed by UPLC-MS.

EXAMPLE 1. DEPROTECTION OF BOC-TRP-ARG(PBF)-OH TO H-TRP-ARG-OH

Starting material: 142 mg of the peptide (96% UPLC purity, 0.185 mmol) per test.
Cleavage time: 90 min.
Reference: 31.7%.
Invention: 68.0% (additional 0.08 mL PhMe and 50 μL TFA, for a total of 13.7 eq TFA, were required for full dissolution).
UPLC-MS: calcd m/z for [M+H]$^+$ 361.20, found m/z 361.2

EXAMPLE 2. DEPROTECTION OF AC-ARG(PBF)-HIS(TRT)-PHE-OH TO AC-ARG-HIS-PHE-OH

Starting material: 369 mg peptide (60% UPLC purity, 0.222 mmol) per test, 180 min
Cleavage time: 180 min
Reference: 65.3%.
Invention: 70.2% (additional 17 μL TFA, for a total of 8.2 eq TFA, were required for full dissolution).
UPLC-MS: calcd m/z for [M+H]$^+$ 501.26, found m/z 501.2.

EXAMPLE 3. DEPROTECTION OF BOC-ARG(MTR)-TYR(TBU)-PHE-OH TO H-ARG-TYR-PHE-OH

Starting material: 234 mg (98% UPLC purity, 0.260 mmol) per test.
Cleavage time: 90 min.
Invention: 84.8%.
Invention: 94.5% (additional 0.12 mL PhMe and 20 μL TFA, for a total of 8.2 eq TFA, were required for full dissolution).
UPLC-MS: calcd m/z for [M+H]$^+$ 485.25, found m/z 485.1.

EXAMPLE 4. DEPROTECTION OF BOC-2NAL-LEU-ARG(PBF)-PHE-OH TO H-2NAL-LEU-ARG-PHE-OH

Starting material: 364 mg (87% UPLC purity, 0.322 mmol) per test.
Cleavage time: 110 min.
Reference: 89.7%.
Invention: 90.5% (additional 24 μL TFA, for a total of 8.2 eq TFA, were required for full dissolution).
UPLC-MS: calcd m/z for [M+H]$^+$ 632.26, found m/z 632.3.

EXAMPLE 5. DEPROTECTION OF AC-ARG(PBF)-MET-M(NO$_2$)TYR-PRO-OH TO AC-ARG-MET-M(NO$_2$)-TYR-PRO-OH

Starting material: 85 mg (96% UPLC purity, 0.089 mmol) per test.
Cleavage time: 90 min.
Reference: 93.6%.
Invention: 95.3% (additional 0.02 mL PhMe and 35 μL TFA, for a total of 12.4 eq TFA, were required for full dissolution).
UPLC-MS: calcd m/z for [M+H]$^+$ 653.27, found m/z 653.2.

EXAMPLE 6. DEPROTECTION OF BOC-RAC-6FTRP-GLY-ARG(PBF)-GLU(OTBU)-OH TO H-RAC-6FTRP-GLY-ARG-GLU-OH

Starting material: 126 mg HPLC-purified peptide (97% UPLC purity, 0.122 mmol) per test.
Cleavage time: 90 min.
Reference: 59.0%.
Invention: 86.8% (additional 0.08 mL PhMe and 35 μL TFA, for a total of 12.4 eq TFA, were required for full dissolution).
UPLC-MS: calcd m/z for [M+H]$^+$ 565.26, found m/z 565.2.

EXAMPLE 7. DEPROTECTION OF BOC-TYR(ET)-ARG(PBF)-ALA-PHE-OH TO H-TYR(ET)-ARG-ALA-PHE-OH

Starting material: 376 mg crude peptide (92% UPLC purity, 0.361 mmol) per test.
Cleavage time: 90 min.
Reference: 86.6%.
Invention: 87.0%. (additional 0.10 mL PhMe and 135 μL TFA, for a total of 12 eq TFA, were required for full dissolution).

EXAMPLE 8. FINAL DEPROTECTION OF AC-5 (OH)TRP-ALA-ARG(PBF)-SER(TBU)-LEU-PHE-OH TO AC-5(OH)TRP-ALA-ARG-SER-LEU-PHE-OH

Starting material: 262 mg (96% UPLC purity, 0.217 mmol) per test.
Cleavage time: 85 min.
Reference: 39.3%.
Invention: 62.9% (additional 0.14 mL PhMe and 272 µL TFA, for a total of 24.1 eq TFA, were required for full dissolution).
UPLC-MS: calcd m/z for [M+H]$^+$ 837.43, found m/z 837.5.

Comparative example C1. Deprotection of Boc-Tyr(Et)-Arg(Pbf)-Ala-Phe-OH to H-Tyr-Arg-Ala-Phe-OH employing a MSA in step a.) to dissolve the peptide
Starting material: 351 mg (93% UPLC purity, 0.309 mmol) per test.
Cleavage time: 110 min.
Reference: 75.8%.
Two-step method: 75.0% UPLC-MS: calcd m/z for [M+H]$^+$ 584.32, found m/z 584.3

As can be retrieved from this comparative example, no improvement of the yield is obtained.

EXAMPLE 9. (TWO-STEP) DEPROTECTION OF BZ-GLY-HIS(TRT)-D-PHE-ARG(PBF)-D-TRP-N(PR)$_2$ TO BZ-GLY-HIS-D-PHE-ARG-D-TRP-N(PR)$_2$ WITH VARYING PARAMETERS

EXAMPLE 9A1. IMPROVED TWO-STEP DEPROTECTION

The protected peptide (0.168 mmol, 93% purity) was given in a vial equipped with stirrer and dissolved in a mixture of 0.63 mL PhMe, 0.09 mL TFA (7.1 eq) and 0.163 mL DDCT (4 eq); the peptide solution was added dropwise to a mixture of 1.51 mL TFA (120 eq) and 0.078 mL MSA (7.1 eq), the vial with the peptide solution was rinsed with 0.07 mL PhMe and rinsing solutions were added to the reaction flask and stirred for 140 min. Results: 90.4%.

EXAMPLE 9A2. IMPROVED TWO-STEP DEPROTECTION WITH REVERSED ADDITION

The protected peptide (0.168 mmol, 93% purity) was given in a round-bottomed flask equipped with stirrer and dissolved in a mixture of 0.70 mL PhMe, 0.09 mL TFA (7.1 eq) and 0.163 mL DDCT (4 eq); to the peptide solution a mixture of 1.51 mL TFA (120 eq) and 0.078 mL MSA (7.1 eq) were added dropwise and stirred for 140 min. Results: 90.8%.

EXAMPLE 9A3. IMPROVED TWO-STEP DEPROTECTION USING 95% TFA(AQ)

The protected peptide (0.168 mmol, 93% purity) was given in a vial equipped with stirrer and dissolved in a mixture of 0.63 mL PhMe, 0.09 mL 95% TFA(aq) (6.8 eq) and 0.163 mL DDCT (4 eq); the peptide solution was added dropwise to a mixture of 1.58 mL 95% TFA(aq) (120 eq) and 0.078 mL MSA (7.1 eq), the vial with the peptide solution was rinsed with 0.07 mL PhMe, rinsing solutions were added to the reaction flask and stirred for 140 min. Results: 89.6%.

EXAMPLE 9A4. IMPROVED TWO-STEP DEPROTECTION WITH DISSOLUTION IN 30% TFA(AQ)

The protected peptide (0.168 mmol, 93% purity) was given in a vial equipped with stirrer and dissolved in a mixture of 0.63 mL PhMe, 0.25 mL 30% TFA(aq) (20 eq) and 0.163 mL DDCT (4 eq); the peptide solution was added dropwise to a mixture of 30% 1.35 mL TFA(aq) (107 eq) and 0.078 mL MSA (7.1 eq), the vial with the peptide solution was rinsed with 0.07 mL PhMe and rinsing solutions were added to the reaction flask and stirred for 140 min. Results: 90.7%.

EXAMPLE 9A5. IMPROVED TWO-STEP DEPROTECTION REPLACING TOLUENE WITH DICHLOROMETHANE

The protected peptide (0.168 mmol, 93% purity) was given in a vial equipped with stirrer and dissolved in a mixture of 0.63 mL DCM, 0.09 mL TFA (7.1 eq) and 0.163 mL DDCT (4 eq); the peptide solution was added dropwise to a mixture of 1.51 mL TFA (120 eq) and 0.078 mL MSA (7.1 eq), the vial with the peptide solution was rinsed with 0.07 mL DCM and rinsing solutions were added to the reaction flask and stirred for 140 min. Results: 91.3%.

EXAMPLE 9A6. IMPROVED TWO-STEP DEPROTECTION WITH DISSOLUTION IN DICHLOROMETHANE/WATER

The protected peptide (0.168 mmol, 93% purity) was given in a vial equipped with stirrer and dissolved in a mixture of 1.30 mL DCM, 24 µL H$_2$O (7.9 eq) and 0.163 mL DDCT (4 eq); to the peptide solution a mixture of 1.60 mL TFA (127 eq) and 0.078 mL MSA (7.1 eq) was added dropwise and stirred for 140 min. Results: 91.5%.

EXAMPLE 9A7. IMPROVED TWO-STEP DEPROTECTION WITH DISSOLUTION IN DICHLOROMETHANE CONTAINING METHANOL

The protected peptide (0.168 mmol, 93% purity) was given in a vial equipped with stirrer and dissolved in a mixture of 1.10 mL DCM, 0.10 mL MeCN, 0.05 mL MeOH (7.3 eq) 0.163 mL DDCT (4 eq) and 0.138 mL TIS (4 eq); to the peptide solution a mixture of 1.60 mL TFA (127 eq) and 0.078 mL MSA (7.1 eq) was added dropwise and stirred for 140 min. Results: 90.2%.

COMPARATIVE EXAMPLE C2A1. TWO-STEP DEPROTECTION USING TIS INSTEAD OF DDCT AS A SCAVENGER

The protected peptide (0.168 mmol, 93% purity) was given in a vial equipped with stirrer and dissolved in a mixture of 0.63 mL PhMe, 0.09 mL TFA (7.1 eq) and 0.140 mL TIS (4 eq); the peptide solution was added dropwise to a mixture of 1.51 mL TFA (120 eq) and 0.078 mL MSA (7.1 eq), the vial with the peptide solution was rinsed with 0.07 mL PhMe, rinsing solutions were added to the reaction flask and stirred for 140 min. Results: 76.4%.

COMPARATIVE EXAMPLE C2A2. TWO-STEP DEPROTECTION USING PHSME INSTEAD OF DDCT AS A SCAVENGER

The protected peptide (0.168 mmol, 93% purity) was given in a vial equipped with stirrer and dissolved in a mixture of 0.63 mL PhMe, 0.09 mL TFA (7.1 eq) and 0.080 mL PhSMe (4 eq); the peptide solution was added dropwise to a mixture of 1.51 mL TFA (120 eq) and 0.078 mL MSA (7.1 eq), the vial with the peptide solution was rinsed with 0.07 mL PhMe, rinsing solutions were added to the reaction flask and stirred for 140 min. Results: 35.1%.

COMPARATIVE EXAMPLE C2A3. TWO-STEP DEPROTECTION USING $H_2O$ ALONE AS A SCAVENGER

The protected peptide (0.168 mmol, 93% purity) was given in a vial equipped with stirrer and dissolved in a mixture of 0.63 mL PhMe, 0.18 mL TFA (14.2 eq) and 0.060 mL $H_2O$ (20 eq); the peptide solution was added dropwise to a mixture of 1.51 mL TFA (120 eq) and 0.078 mL MSA (7.1 eq), the vial with the peptide solution was rinsed with 0.07 mL PhMe, rinsing solutions were added to the reaction flask and stirred for 140 min. Results: 85.4%.

COMPARATIVE EXAMPLE C2A4. TWO-STEP DEPROTECTION WITH DISSOLUTION IN THF INSTEAD OF PHME

The protected peptide (0.168 mmol, 93% purity) was given in a vial equipped with stirrer and dissolved in a mixture of 0.63 mL THF, 0.09 mL TFA (7.1 eq) and 0.163 mL DDCT (4 eq); the peptide solution was added dropwise to a mixture of 1.51 mL TFA (120 eq) and 0.078 mL MSA (7.1 eq), the vial with the peptide solution was rinsed with 0.07 mL THF, rinsing solutions were added to the reaction flask and stirred for 140 min. Results: 31.7%.

COMPARATIVE EXAMPLE C2A5. TWO-STEP DEPROTECTION WITH DISSOLUTION IN DMSO INSTEAD OF PHME

The protected peptide (0.168 mmol, 93% purity) was given in a vial equipped with stirrer and dissolved in a mixture of 0.63 mL DMSO, 0.09 mL TFA (7.1 eq) and 0.163 mL DDCT (4 eq); the peptide solution was added dropwise to a mixture of 1.51 mL TFA (120 eq) and 0.078 mL MSA (7.1 eq), the vial with the peptide solution was rinsed with 0.07 mL DMSO, rinsing solutions were added to the reaction flask and stirred for 140 min. Results: 2.9%.

COMPARATIVE EXAMPLE C2A6. TWO-STEP DEPROTECTION WITH DISSOLUTION IN ACOET INSTEAD OF PHME

The protected peptide (0.168 mmol, 93% purity) was given in a round-bottomed flask equipped with stirrer and dissolved in a mixture of 0.70 mL AcOEt, 0.09 mL TFA (7.1 eq) and 0.163 mL DDCT (4 eq); the peptide solution was added dropwise to a mixture of 1.51 mL TFA (120 eq) and 0.078 mL MSA (7.1 eq), the vial with the peptide solution was rinsed with 0.07 mL AcOEt, rinsing solutions were added to the reaction flask and stirred for 140 min. Results: 61.8%.

COMPARATIVE EXAMPLE C2A7. TWO-STEP DEPROTECTION USING PURE MSA FOR THE CLEAVAGE SOLUTION

The protected peptide (0.168 mmol, 93% purity) was given in a round-bottomed flask equipped with stirrer and dissolved in a mixture of 0.75 mL PhMe, 0.40 mL 95% TFA(aq) (30 eq) and 0.163 mL DDCT (4 eq); to the peptide solution 0.22 mL MSA (20 eq) were added dropwise, the resulting mixture was stirred for 140 min. Results: 38.8%.

EXAMPLE 9A8. IMPROVED TWO-STEP DEPROTECTION WITH ACOH AS ACID IN THE PEPTIDE SOLUTION

The protected peptide (0.173 mmol, 96% purity) was given in a vial equipped with stirrer and dissolved in a mixture of 0.63 mL PhMe, 0.072 mL AcOH (7.2 eq) and 0.167 mL DDCT (4 eq). The peptide solution was added dropwise under stirring to a mixture of 1.56 mL TFA (120 eq) and 0.081 mL MSA (7.1 eq); the vial with the peptide solution was rinsed with 0.07 mL PhMe, rinsing solutions were added to the reaction flask and stirred for 140 min. Results: 92.0%.

EXAMPLE 9A9. IMPROVED TWO-STEP DEPROTECTION WITH USING ETOH AS PROTIC CO-SOLVENT

The protected peptide (0.173 mmol, 96% purity) was given in a round-bottomed flask equipped with stirrer and dissolved in a mixture of 1.1 mL PhMe, 0.10 mL EtOH and 0.167 mL DDCT (4 eq). To the peptide solution a mixture of 1.65 mL TFA (127 eq) and 0.081 mL MSA (7.1 eq) was added dropwise under stirring and stirred for 140 min. Results: 90.8%.

COMPARATIVE EXAMPLE C2A8. TWO-STEP DEPROTECTION—NO APROTIC SOLVENT

The protected peptide (0.173 mmol, 96% purity) was given in a vial equipped with stirrer and dissolved in a mixture of 0.63 mL AcOH (63 eq), 25 μL $H_2O$ (8 eq) and 0.167 mL DDCT (4 eq). The peptide solution was added dropwise under stirring to a mixture of 1.65 mL TFA (127 eq) and 0.081 mL MSA (7.1 eq); the vial with the peptide solution was rinsed with 0.07 mL AcOH (7 eq), rinsing solutions were added to the reaction flask and stirred for 140 min. Results: 65.6%.

The invention claimed is:

1. A method for deprotecting a peptide selected from the group consisting of Boc-Trp-Arg(Pbf)-OH, Ac-Arg(Pbf)-His(Trt)-Phe-OH, TFA-H-Tyr(tBu)-Arg(Pbf)-Pro-OH, Boc-rac-6FTrp-Gly-Arg(Pbf)-Glu(OtBu)-OH, Boc-Tyr(Et)-Arg(Pbf)-Ala-Phe-OH, Ac-5-(OH)Trp-Ala-Arg(Pbf)-Ser(tBu)-Leu-Phe-OH, Boc-Arg(Mtr)-Tyr(tBu)-Phe-OH, Boc-2Nal-Leu-Arg(Pbf)-Phe-OH, Ac-Arg(Pbf)-Met-m($NO_2$)Tyr-Pro-OH and Bz-Gly-His(Trt)-D-Phe-Arg(Pbf)-D-Trp-N(Pr)$_2$, wherein the method comprises the steps of:
 (a) solubilizing the peptide in a solvent mixture of at least one aprotic organic solvent, a thiol scavenger, and either a protic solvent or a carboxylic acid selected from the group of formic acid, acetic acid and/or trifluoroacetic acid or a mixture thereof, wherein the carboxylic acid is present in an amount of 5 to 30%, based on the total volume of the solvent mixture, followed by
 (b) mixing the solution obtained in step (a) with a mixture of (i) a carboxylic acid selected from the group consisting of formic acid, acetic acid and trifluoroacetic acid, and (ii) a sulfonic acid selected from the group consisting of methanesulfonic acid, trifluoromethane sulfonic acid, benzene sulfonic acid and p-toluene sulfonic acid, wherein a total molar amount of the carboxylic acid used in steps (a) and (b) is higher than a total molar amount of the sulfonic acid.

2. The method according to claim 1, wherein the at least one aprotic organic solvent in step (a) is selected from the group consisting of aromatic hydrocarbons which are liquid at ambient temperature, $C_{1-6}$-halogenoalkanes and acetonitrile and mixtures thereof.

3. The method according to claim 1, wherein the aprotic solvent in step (a) is present in an amount of 1 to 100 mL/g peptide.

4. The method according to claim 1, wherein the protic solvent in step (a) is selected from the group consisting of water, an alcohol and mixtures thereof.

5. The method according to claim 1, wherein the thiol scavenger is an aliphatic thiol.

6. The method according to claim 1, wherein step (a) is conducted at a temperature of 15 to 25° C.

7. The method according to claim 1, wherein the sulfonic acid in step (b) is present in an amount of 1 to 20 mol-equivalents, based on each protected arginine moiety present in the peptide.

8. The method according to claim 1, wherein a molar ratio of the total amount acid of the carboxylic acid used in steps (a) and (b) to the molar amount of the sulfonic acid used in step (b) is 100:1 to 10:1.

9. The method according to claim 1, wherein the aprotic solvent in step (a) is present in an amount of 2 to 10 mL/g peptide.

10. The method according to claim 1, wherein the aprotic solvent in step (a) is present in an amount of 2.5 to 7 mL/g peptide.

11. The method according to claim 1, wherein the protic solvent in step (a) is selected from the group consisting of water, a $C_{1-4}$-alkyl alcohol and mixtures thereof.

12. The method according to claim 1, wherein the thiol scavenger is dodecanethiol.

13. The method according to claim 1, wherein the sulfonic acid in step (b) is present in an amount of 2 to 12 mol-equivalents, based on each protected arginine moiety present in the peptide.

14. The method according to claim 1, wherein the sulfonic acid in step (b) is present in an amount of 3 to 10 mol-equivalents, based on each protected arginine moiety present in the peptide.

15. The method according to claim 1, wherein the sulfonic acid in step (b) is present in an amount of 5 to 8 mol-equivalents, based on each protected arginine moiety present in the peptide.

16. The method according to claim 1, wherein the sulfonic acid used in step (b) is methane sulfonic acid.

17. The method according to claim 8, wherein the molar ratio of the total amount acid of the carboxylic acid used in steps (a) and (b) to the molar amount of the sulfonic acid used in step (b) is 50:1 to 12:1.

18. The method according to claim 8, wherein the molar ratio of the total amount acid of the carboxylic acid used in steps (a) and (b) to the molar amount of the sulfonic acid used in step (b) is 30:1 to 15:1.

19. The method according to claim 8, wherein the molar ratio of the total amount acid of the carboxylic acid used in steps (a) and (b) to the molar amount of the sulfonic acid used in step (b) is 25:1 to 18:1.

* * * * *